United States Patent
Martin et al.

(10) Patent No.: US 8,093,307 B2
(45) Date of Patent: Jan. 10, 2012

(54) SILANE COMPOUNDS CARRYING A HYDRAZONE OR DIAZO FUNCTIONAL GROUP IN ORDER TO FUNCTIONALIZE SOLID SUPPORTS AND IMMOBILIZE BIOLOGICAL MOLECULES ON THESE SUPPORTS

(75) Inventors: Franck Martin, Montpellier (FR); Antoine Hoang, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 677 days.

(21) Appl. No.: 12/299,968

(22) PCT Filed: May 18, 2007

(86) PCT No.: PCT/EP2007/054830
§ 371 (c)(1),
(2), (4) Date: Nov. 7, 2008

(87) PCT Pub. No.: WO2007/135096
PCT Pub. Date: Nov. 29, 2007

(65) Prior Publication Data
US 2009/0208374 A1    Aug. 20, 2009

(30) Foreign Application Priority Data
May 19, 2006  (FR) ...................................... 06 51842

(51) Int. Cl.
*C08G 61/04*    (2006.01)
(52) U.S. Cl. .......... 520/1; 427/2.13; 427/2.1; 427/207.1
(58) Field of Classification Search .................... 430/17; 427/2.13
See application file for complete search history.

(56) References Cited

U.S. PATENT DOCUMENTS 3,905,816 A * 9/1975 Boardman et al. .............. 430/17

FOREIGN PATENT DOCUMENTS

JP    63 235935    9/1988

OTHER PUBLICATIONS

International Search Report completed Aug. 30, 2007, in International Application No. PCT/EP2007/054830, filed May 18, 2007.
French Search Report dated Jan. 15, 2007, prepared in French Patent Application No. 06 51842, filed May 19, 2006.
Kanoh, Naoki, "Development of small molecule microarrays", Database Caplus, Chemical Abstracts Service, STN CA Caesar Accession No. 1849—XP 002414763, Search Report.
Barnes-Seeman, David, et al., "Expanding the Functional Group Compatibility of Small-Molecule Microarrays: Discovery of Novel Calmodulin Ligands", Angew. Chem. Int. Ed., 2003, p. 2376-2379, vol. 42, Search Report.

* cited by examiner

*Primary Examiner* — Dah-Wei Yuan
*Assistant Examiner* — Andrew Bowman
(74) *Attorney, Agent, or Firm* — Brinks, Hofer, Gilson & Lione

(57) ABSTRACT

The invention relates to novel silane compounds corresponding to the following formula (I):

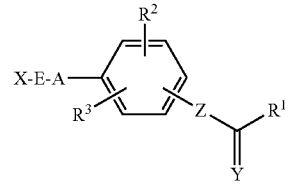

in which $R^1$ can represent a methyl group, $R^2$ and $R^3$ can represent a hydrogen atom, A can represent —O—, E can represent an alkylene group, X can represent a methoxysilane group, Z can represent a simple bond and Y can represent an —$N_2$ or —N—$NH_2$ group.
Use of these silane compounds to functionalize solid supports and to immobilize biological molecules on these supports.

11 Claims, No Drawings

SILANE COMPOUNDS CARRYING A HYDRAZONE OR DIAZO FUNCTIONAL GROUP IN ORDER TO FUNCTIONALIZE SOLID SUPPORTS AND IMMOBILIZE BIOLOGICAL MOLECULES ON THESE SUPPORTS

This application is a National Stage application of International Application No. PCT/EP2007/054830, filed May 18, 2007, the entire contents of which is hereby incorporated herein by reference. This application also claims the benefit under 35 U.S.C. §119 of French Patent Application No. 06 51842, filed May 19, 2006, the entire contents of which is hereby incorporated herein by reference.

TECHNICAL FIELD

The present invention relates to novel silane compounds carrying a hydrazone or diazo functional group which can be used to functionalize solid supports, to supports functionalized by the said silane compounds and to their uses in the immobilization of biological molecules, in particular nucleic acids.

The analysis of the structure, of the organization and of the sequence of a molecule of nucleic acid is of major importance in the production, diagnosis and treatment of disease, in forensic medicine, in epidemiology and public health and in the elucidation of the factors which control gene expression and development.

Supports carrying immobilized biological molecules, such as nucleic acids, are advantageously used for the detection and recognition of biological entities, but also for other applications, such as the separation and purification of biological molecules.

In order to do this, it is essential to have available functionalized solid supports exhibiting the following characteristics:
  making possible the reproducible immobilization of the biological molecules of interest;
    making possible the immobilization of the biological molecules of interest in a sensitive way, the sensitivity of a functionalized solid support depending on the degree of immobilization and on the method of detection of a signal but also on the level of background noise;
  being reusable.

The immobilization of biological molecules of interest on solid supports is generally carried out in two stages:
  a first stage of functionalization of the supports, which consists of a chemical modification of their surface by grafting coupling agents which will provide for the attaching of the biological molecules to the support;
  a second stage of immobilization which consists in establishing an interaction between the biological molecules and the coupling agents grafted to the support, it being possible for the interaction to consist of the formation of a covalent bond between the biological molecule and the coupling agent or of weaker bonds (such as electrostatic interactions or dative bonds).

The coupling agents are grafted to the surface of the supports by reaction of the —OH or hydride functional groups of the support and of the reactive functional groups of the agent, to form strong ionic or covalent interactions between the coupling agent and the support, and are organized at the surface of the support generally in the form of a dense monolayer organized at the surface, for example, by formation of bonds of the Van der Waals type between the grafted molecules of coupling agents.

Generally, in order to attach biological molecules of the nucleic acid type, it is necessary to modify these molecules beforehand by introduction of a reactive group capable of reacting with either the support directly or the coupling agent. However, the use of such modified molecules considerably increases the cost of implementing the processes for the immobilization of these molecules.

The inventors thus set themselves the aim of providing novel silane compounds capable of being grafted to the surface of a solid support and comprising groups which make possible the direct immobilization of biological molecules by the formation of covalent bonds without requiring preliminary modification of the said molecules.

ACCOUNT OF THE INVENTION

Thus, the invention relates, according to a first subject-matter, to a silane compound corresponding to the following formula (I):

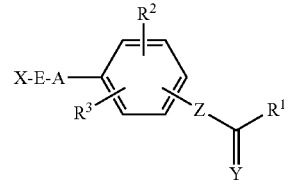

in which:
  $R^1$ represents a hydrogen atom, an alkyl group or an aryl group;
  $R^2$ and $R^3$ represent, independently of one another, H, $NO_2$, Cl, Br, F, I, OR, SR, $NR_2$, R, NHCOR, CONHR or COOR with R representing an alkyl or aryl group;
  Z represents a simple bond or an organic spacer group comprising at least one double bond capable of making possible the conjugation of the double bond carrying the Y group and of the aromatic ring;
  X represents a silyl group capable of creating a covalent bond after reaction with the hydroxyl or hydride functional groups of a support;
  E represents an organic spacer group;
  A represents a simple bond or a group chosen from —CONH—, —NHCO—, —O— or —S—;
  Y represents an $=N_2$ or $=N$—$NH_2$ group.

According to the invention, the E group is an organic spacer group, its essential role being to confer specific properties on the film resulting from the grafting of the silane compounds to the surface of a support.

This E group is generally a hydrocarbon group comprising, for example, from 2 to 24 carbon atoms and optionally comprising one or more unsaturations and/or one or more aromatic groups and/or one or more heteroatoms.

By way of examples, the E group can be an alkylene group, that is to say a sequence of the —$CH_2$-type comprising, for example, from 8 to 24 carbon atoms. This type of group confers, on the silane compounds, once grafted to a support, an ability to interact with one another by creation of interchain interactions and thus contributes to the production of organized monolayers.

The E group can be a fluoroalkylene group comprising from 3 to 24 carbon atoms. These groups contribute to conferring, on the film resulting from the grafting of the silane compounds comprising them, properties which allow them to be used in chromatography and in electrophoresis.

The E group can be a hydrocarbon group comprising one or more unsaturations, for example of the acetylenic type. An example of such a group can be an alkylene group as defined above interrupted by one or more acetylenic unsaturations. When the E group comprises at least two unsaturations, it can confer on the silane compounds, once grafted to a support, an ability to crosslink.

The E group can also be a hydrocarbon group comprising one or more aromatic groups.

Mention may be made, for example, of a group comprising aromatic groups conjugated with unsaturated linear groups, such as a group resulting from the sequence of a phenylene-vinylene or phenylene-acetylene unit. These groups contribute to conferring, on the film resulting from the grafting of the silane compounds comprising them, non-linear optical properties.

Mention may be made, for example, of a group comprising pyrrole or thiophene units. These groups contribute to conferring, on the film resulting from the grafting of the silane compounds comprising them, electron-conduction properties.

Mention may be made, for example, of a group comprising one or more aromatics substituted by one or more heteroatomic groups, such as a group comprising a sequence of quinone units or of diazo units. These groups contribute to conferring, on the film resulting from the grafting of the silane compounds comprising them, photo/electroluminescence properties.

According to the invention, X represents a silyl group which makes possible the covalent attachment of the silane compound to the hydroxyl or hydride functional groups of a support, which support can, for example, be a solid support made of silicon, of ITO (indium tin oxide) or of titanium.

This X group can, for example, be a trihalosilane group (such as a trifluorosilane group or a trichlorosilane group); a trihydrosilane group; a trialkoxysilane group —Si(OR$^4$)$_3$ with R$^4$ representing a saturated, linear or branched, C$_1$ to C$_6$ alkyl group or a phenyl group (such as a trimethoxysilane group, a triethoxysilane group or a triisopropoxysilane group); a triaminoalkoxyamine group —Si(NR$^5$R$^6$)$_3$ with the R$^5$ and R$^6$ groups independently representing a saturated, linear or branched, C$_1$ to C$_6$ alkyl group or a phenyl group; an organometallic group (such as an organomagnesium group or an organolithium group); or a hydrolysable group.

Z can be a simple bond, in which case the hydrazone or diazo functional group can be conjugated directly with the adjacent aromatic ring, or Z can be an organic group comprising at least one double bond which makes possible conjugation between the aromatic ring and the hydrazone or diazo functional group. The term "conjugation" is to be understood to mean the delocalisation of the electrons of the aromatic ring along the carbon chain of the organic group. This organic group can be a group of formula:

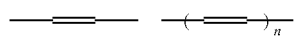

n being an integer corresponding to the repeat number of the unit placed between brackets, it being possible for n to be equal to 1 or 2.

R$^1$ can be an alkyl group comprising, for example, from 1 to 10 carbon atoms, such as a methyl group, or an aryl group comprising, for example, from 6 to 18 carbon atoms, such as a phenyl group.

A can be a simple bond, in which case the aromatic ring will be connected directly to the E group. A can also be a —CONH—, —NHCO—, —S— or —O— group.

A first family of compounds in accordance with the invention is a family in which Y is a group of formula —N—NH$_2$, in which case these compounds correspond to the following formula (II):

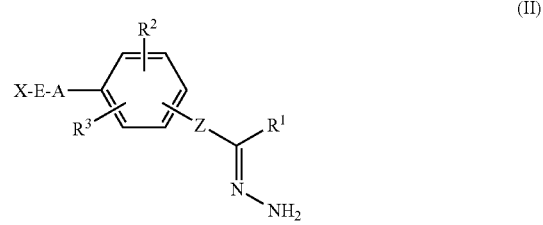

(II)

Specific compounds coming within the definition of this family are those for which A corresponds to —O—, and E represents an alkylene group comprising from 8 to 24 carbon atoms and Z is a simple bond, R$_2$, R$_3$, R$_1$ and X being as defined above.

Mention may be made, for example, of the compound of following formula (III):

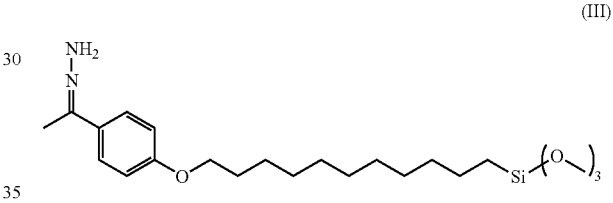

(III)

A second family of compounds in accordance with the invention is a family in which Y is a group of formula —N$_2$, in which case these compounds correspond to the following formula (IV):

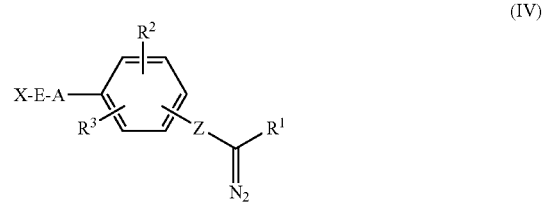

(IV)

Specific compounds coming within the definition of this family are those for which A corresponds to —O—, E represents an alkylene group comprising from 8 to 24 carbon atoms and Z is a simple bond, R$_2$, R$_3$, R$_1$ and X being as defined above.

Mention may be made, for example, of the compound of following formula (V):

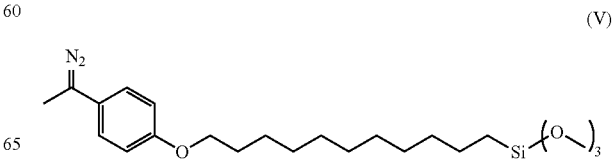

(V)

The compounds of the invention can be prepared by conventional synthetic methods accessible to an expert whose is a specialist in organic synthesis.

By way of example, in order to obtain compounds for which E is an alkylene group, A is —O— and X is an —Si(OR⁴)₃ group, the preparation can be envisaged in three stages according to the following reaction scheme.

1) Reaction of a phenolic carbonyl compound with a halogenated vinyl precursor compound

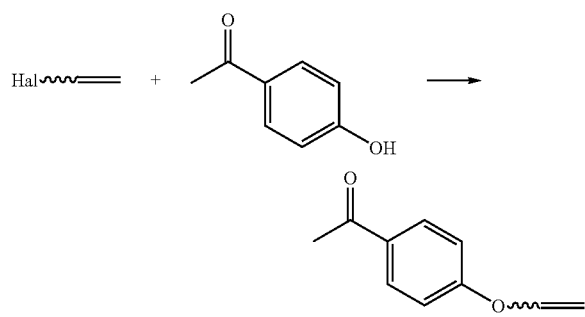

This reaction consists of a nucleophilic substitution of the halogen atom Hal.

The wavy bond between Hal and =represents a hydrocarbon group connecting Hal and =, such as an alkylene group.

2) The compounds obtained on conclusion of stage 1 are subsequently subjected to a reaction for the formation of the hydrazone functional group by reaction with a hydrazine solution according to the following reaction scheme:

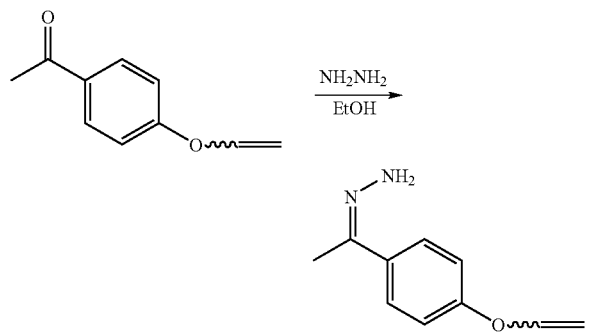

3) The compounds obtained on conclusion of stage 2 are subsequently subjected to a hydrosilylation reaction with a reactant of the HSi(OR⁴)₃ type in the presence of a Karstedt catalyst Pt[Si(CH₃)₂HC=CH₂]₂O according to the following reaction scheme:

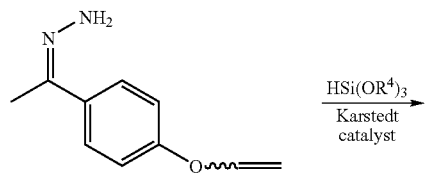

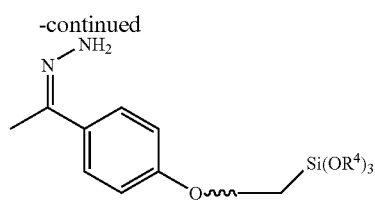

Finally, the hydrazone functional group obtained above can be converted to a diazo functional group by an oxidation reaction, for example with manganese oxide MnO₂.

A person skilled in the art will adapt these reaction schemes according to the silane compounds which he wishes to obtain.

As mentioned above, the silane compounds of the invention are capable of being grafted to the surface of a support due to the presence of the X group suitable for reacting with hydroxyl or hydride functional groups (present on the support) to form covalent bonds.

Thus, the invention relates, according to a second subject-matter, to a process for the functionalization of a solid support comprising hydroxyl or hydride functional groups at the surface, comprising a stage in which a solution comprising at least one silane compound as defined above is brought into contact with the said support.

This process can comprise, beforehand, a stage of treatment of the surface of support in order to create, on the said surface, the hydroxyl or hydride functional groups necessary for the grafting.

Thus, for a support made of silicon 100 (for example of the wafer type), it is preferable, before functionalization, to treat the latter by bringing it into contact with a sodium hydroxide solution in order to generate silanol functional groups.

The supports which can be functionalized according to the process of the invention can be organic supports (for example made of plastics), inorganic supports, for example supports made of metal oxide (for example, silica and its derivatives, such as glass, quartz, indium tin oxide, and the like), metal supports (such as titanium supports) or supports made of silicon, the essential point being that these supports are capable (optionally with the pre-treatment stage mentioned above) of exhibiting hydroxyl or hydride functional groups for the grafting of the silane compounds of the invention.

Another subject-matter of the invention is the functionalized solid support capable of being obtained by the process of the invention.

Due to the nature of the Y group, the grafted silane compounds have the ability to interact with biological molecules in order to immobilize them.

Another subject-matter of the present invention is thus a method for the immobilization of biological molecules on a functionalized solid support, comprising the following stages:

a) a stage of employing the process of functionalization of the support as defined above;

b) a stage in which the support obtained in stage a) is brought into contact with a solution comprising the biological molecule(s) to be immobilized.

The molecules to be immobilized can be oligonucleotides, nucleic acids, polypeptides (proteins, enzymes), lipids, carbohydrates or hormones, in particular molecules comprising phosphate groups capable of reacting with a diazo functional group to form a covalent bond.

Within the meaning of the present invention and in what follows, the term "nucleic acids" is understood to mean both oligonucleotides and DNAs or RNAs.

Another subject-matter of the invention is the solid supports obtained by employing the method of immobilization in accordance with the invention, that is to say the solid supports on which the biological molecules of interest are immobilized by covalent attachment.

These solid supports can thus be used as analytical tools (for example, for a diagnosis or a sequencing) or as synthetic tools for producing, for example, coatings.

The supports thus find applications in numerous fields, such as synthesis on solid supports, the separation and purification of molecules (electrophoresis and chromatography), or biosensors.

The use of functionalized solid supports according to the present invention makes it possible to immobilize different types of biological molecules and thus to prepare different types of chips, such as nucleic acid chips, for example DNA chips, or polypeptide chips, for example protein chips.

The use of modified solid supports according to the present invention is particularly advantageous in the preparation of DNA chips, namely supports on which oligo- or polynucleotides of known sequences are covalently attached. Such DNA chips make it possible, by hybridization of the oligo- or polynucleotides immobilized on the support with target nucleic acids or oligonucleotides, to determine the sequence of these target molecules and to follow the expression of the genes. It is specified that the term "DNA chip" is to be understood to mean a solid support of reduced size where a multitude of capture probes are attached at predetermined positions.

Another subject-matter of the present invention is thus a nucleic acid or polypeptide chip obtained by the immobilization method of the invention mentioned above.

The invention will now be described with reference to the following examples, given by way of illustration and without limitation.

ACCOUNT OF SPECIFIC EMBODIMENTS

Example 1

This example illustrates the preparation of a silane compound in accordance with the invention: 11-(p-phenylmethylhydrazone)undecyltrimethoxysilane, according to the following reaction scheme:

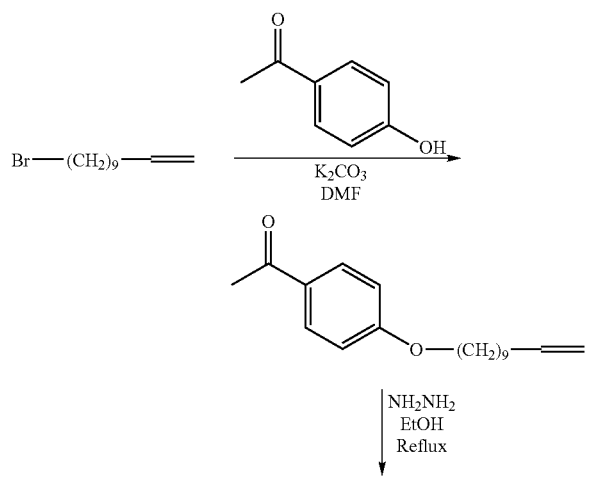

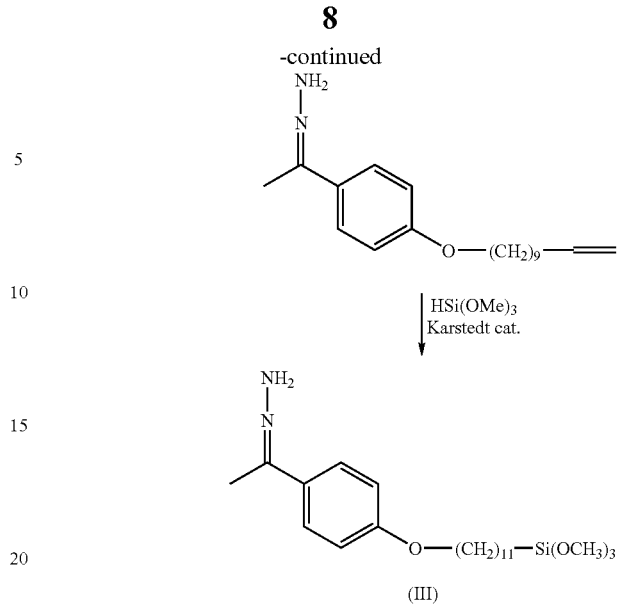

The acetophenone functional group is incorporated by a reaction of the Williamson type between 11-bromoundecene and 4-hydroxyacetophenone. The hydrazone group is synthesised by reaction in hydrazine under hot conditions. The silyl part is incorporated after a hydrosilylation reaction in the presence of the Karstedt catalyst.

a) Stage 1: Synthesis of 11-(p-acetophenone)undec-1-ene

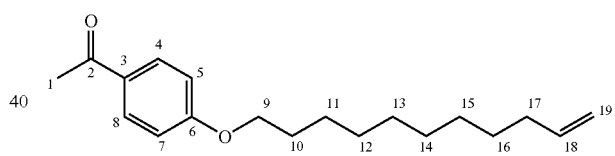

11-Bromoundecene (95%) (15.54 g, 14.5 ml, 63 mmol) and potassium carbonate (8.74 g, 63 mmol, 1 eq.) are added to a solution of 4-hydroxyacetophenone (8.79 g, 63 mmol, 1 eq.) dissolved in 150 ml of DMF. The reaction is carried out at 50° C. for 16 hours. After the evaporation of the DMF and taking up the residue in ethyl ether, the reaction mixture is successively washed with deionized water (three times) and with a saturated sodium chloride solution, dried over anhydrous magnesium sulphate and then concentrated. The residue is purified by chromatography on a column of silica gel (cyclohexane→cyclohexane/ethyl acetate (75/25)) to give a white solid.

The characteristics of the product obtained are as follows:

Weight obtained: 14.46 g

Yield: 79%

Melting point: 35-40° C.

$^1$H NMR (200 MHz, CDCl$_3$): 1.31 (12H, m, H$^{11-16}$), 1.80 (2H, m, H$^{10}$), 2.04 (2H, m, H$^{17}$), 2.56 (3H, s, H$^1$), 4.02 (2H, t, H$^9$, $^3J_{H-H}$=6.5 Hz), 4.97 (2H, m, H$^{19}$), 5.82 (1H, m, H$^{18}$), 6.92 (2H, d, H$^{5+7}$, $^3J_{H-H}$=9 Hz), 7.93 (2H, d, H$^{4+8}$, $^3J_{H-H}$=8.8 Hz)

$^{13}$C NMR (200 MHz, CDCl$_3$): 26.38, 26.77 (H$^1$), 29.33, 29.51 (2C), 29.75, 29.82, 29.91, 34.23, 68.67 (C$^9$), 114.55 (C$^{5+9+19}$), 130.5 (C$^3$), 131.01 (C$^{4+8}$), 139.63 (C$^{18}$), 163.55 (C$^6$), 197.29 (C$^2$)

b) Stage 2: Synthesis of 11-(p-phenylmethyl-hydrazone)undec-1-ene

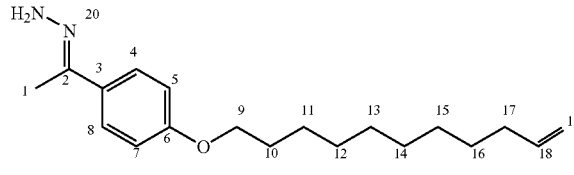

Hydrazine monohydrate (20.34 g, 20.2 ml, 408 mmol, 8.1 eq.) is added to a solution of 4-(11-undec-1-ene)acetophenone (14.46 g, 69 mmol) dissolved in 200 ml of ethanol. The reaction is carried out at reflux for 12 hours and then the solution is cooled to −20° C. The precipitate formed is filtered off to give a white solid.

The characteristics of the product obtained are as follows:
Weight obtained: 14.54 g
Yield: 96%

$^1$H NM (200 MHz, CDCl$_3$): 1.30 (12H, m, H$^{11-6}$), 1.76 (2H, m, H$^{10}$), 2.04 (2H, m, H$^{17}$), 2.12 (3H, s, H$^1$), 3.96 (2H, t, H$^9$; $^3J_{H-H}$=6.6 Hz), 4.97 (2H, m, H$^{19}$), 5.24 (1H, S, H$^{20}$), 5.82 (1H, m, H$^{18}$), 6.87 (2H, d, H$^{5+7}$, $^3J_{H-H}$=9 Hz), 7.57 (2H, d, H$^{4+8}$, $^3J_{H-H}$=9 Hz)

$^{13}$C NMR (200 MHz, CDCl$_3$): 12.17 (H$^1$), 26.44, 29.34, 29.54, 29.66, 29.80, 29.84, 29.93, 34.23, 68.42 (C$^9$), 114.62 (C$^{5+7+19}$), 127.19 (C$^3$), 132.23 (C$^{4+8}$), 139.63 (C$^{18}$), 148.21 (C$^2$), 159.67 (C$^6$)

m/z (NBA): 303 [M+H]$^+$ c) Stage 3: Synthesis of 11-(p-phenylmethyl-hydrazone)undecyltrimethoxysilane (III)

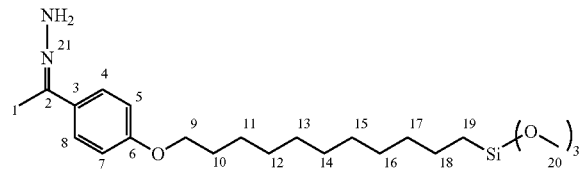

11-(p-phenylmethylhydrazone)undec-1-ene (4 g, 13 mmol) is mixed with trimethoxysilane (90%) (2.62 g, 2.7 ml, 19 mmol, 1.5 eq.). The Karstedt catalyst (0.31 g, 0.03 mmol, 0.0025 eq.) is added very slowly. The reaction takes place at ambient temperature for 16 hours. After evaporating the excess trimethoxysilane, the crude reaction product is dissolved in anhydrous pentane and cooled to −20° C. The entire mixture is filtered to give a yellow solid.

The characteristics of the product obtained are as follows:
Weight obtained: 2.6 g
Yield: 46%

$^1$H NMR (200 MHz, CDCl$_3$): 0.66 (2H, m, H$^{19}$), 1.28 (12H, m, H$^{10}$), 1.78 (2H, m, H$^{10}$), 2.32 (2H, m, H$^1$), 3.57 (9H, 5, H$^{20}$), 3.99 (2H, t, H$^9$, $^3J_{H-H}$=6.5 Hz), 6.92 (2H, d, H$^{5+7}$, $^3J_{H-H}$=9 Hz), 7.86 (2H, d, H$^{4+8}$, $^3J_{H-H}$=9 Hz)

$^{13}$C NMR (200 MHz, CDCl$_3$): 9.55 (H$^{19}$), 15.20 (H$^1$), 23.02, 26.46, 29.68 (2C), 29.83, 29.94, 29.99, 30.02, 33.58, 50.93 (3C, C$^{20}$), 68.49 (C$^9$), 114.58 (C$^{5+7}$), 128.45 (C$^{4+8}$), 131.51 (C$^3$), 158.27 (C$^2$), 160.82 (C$^6$)

m/z (NBA): 425 [M+H]$^+$ d) Silanization by the Compound (III) of a Support Made of Silicon The hydroxylation of the substrate made of silicon covered with a layer of thermal oxide with a thickness of 5000 Å is carried out in a 3.5M sodium hydroxide solution for 2 hours with stirring. The support is subsequently rinsed successively with deionized water and ethanol under ultrasound (4 minutes each).

A silanizing solution with a concentration of 10$^{-2}$M in anhydrous trichloroethylene is used and the silanization reaction is carried out at a controlled temperature of 2° C. for 24 h. The support is subsequently rinsed successively with dichloromethane, ethanol and chloroform under ultrasound (4 minutes each).

The diazo functional group is obtained during a post-silanization reaction of the modified support with a solution of activated MnO$_2$ dissolved in dimethylformamide for 30 minutes. The support is subsequently rinsed with dimethylformamide under ultrasound (4 minutes each).

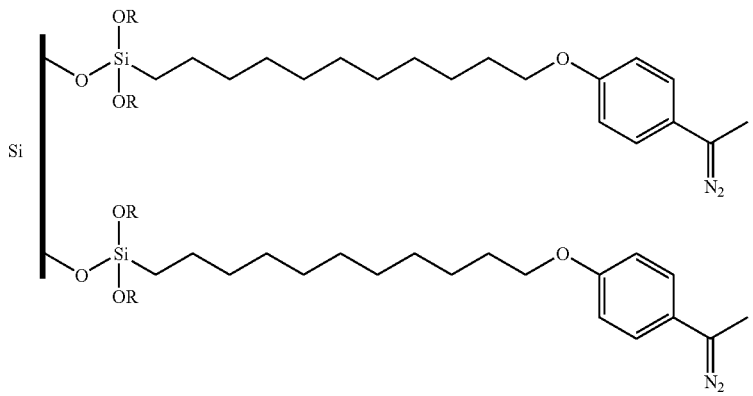

R representing CH$_3$.

Example 2

This example illustrates the immobilization of an oligonucleotide on the modified substrate according to Example 1 above and the hybridization of this oligonucleotide with a complementary target.

a) Immobilization of the Oligonucleotide on the Modified Substrate

After activation of the solid support by oxidation with $MnO_2$, 2 blocks of 3 lines, each comprising 3 spots of nucleic acids, are formed from depositions carried out manually using a micropipette with a deposited volume of 0.2 µl for each spot.

The upper block corresponds to the PNA and the lower to the ODN (oligonucleotide) with the same sequence of nucleic bases (5'-GAT AAA CCC ACT CTA-3') and with the same concentration of 10 µM in 0.3M citrate buffer with a pH of 9. The difference between the PNA and the ODN lies in the fact that the PNA corresponds to a sequence of nucleic acids as defined above connected via a peptide backbone, while the ODN corresponds to the same sequence of nucleic acids but connected via a phosphodiester backbone.

b) Post-Immobilization Treatment

After deposition, the solid support is placed in a hermetically closed humid chamber and left for approximately 16 hours. It is subsequently rinsed with water, then with 0.2% SDS (sodium dodecyl sulphate) detergent and then again with water, with a duration of 10 minutes for each washing stage.

c) Hybridization

Subsequently, the visualization of the spots of nucleic acids deposited on the solid support is carried out by the surface hybridization stage for one hour at 40° C. with a solution of DNA with the complementary sequence (5'-TAG AGT GGG TTT ATC-3') carrying the CY3 fluorophore group diluted to 20 nM in a commercial hybridization buffer (Hyb buffer solution, Sigma Aldrich ref: H7140) based on sodium citrate. The solid support is subsequently rinsed with 0.2× sodium citrate (X representing, for the sodium citrate, $15\times10^{-3}$ $mol.L^{-1}$) for 5 minutes.

d) Reading and Results

The fluorescence signals are obtained on a scanner sold under the name GenePix® by AXON.

Only the spots of the lower block emit a fluorescence, which testifies to the specificity of the reaction between the phosphate functional groups of the phosphodiester backbone of the oligonucleotide ODN and the surface aryldiazomethane functional group. The spots of the upper block do not emit fluorescence, owing to the fact that the PNAs were not immobilized at the surface of the substrate, it not being possible for the peptide groups of their backbone to react with the surface aryldiazomethane functional groups. A good homogeneity between the fluorescence results was also observed.

The invention claimed is:

1. A silane compound corresponding to either of the following formulae:

(II)

(IV)

wherein:
- $R^1$ represents a hydrogen atom, an alkyl group or an aryl group;
- $R^2$ and $R^3$ represent, independently of one another, H, $NO_2$, Cl, Br, F, I, OR, SR, $NR_2$, R, NHCOR, CONHR or COOR, with R representing an alkyl or aryl group;
- Z represents a simple bond;
- X represents a silyl group capable of creating a covalent bond after reaction with the hydroxyl or hydride functional groups of a support;
- E represents an alkylene group comprising from 8 to 24 carbon atoms; and
- A represents —O—.

2. The compound of claim 1, wherein X represents a trihalosilane group; a trihydrosilane group; a trialkoxysilane group —$Si(OR^4)_3$, with $R^4$ representing a saturated, linear or branched, $C_1$ to $C_6$ alkyl group or a phenyl group; a triaminoalkoxyamine group —$Si(NR^5R^6)_3$, with the $R^5$ and $R^6$ groups independently representing a saturated, linear or branched, $C_1$ to $C_6$ alkyl group or a phenyl group; or an organometallic group.

3. The compound of claim 1, corresponding to the following formula (III):

(III)

4. The compound of claim 1, corresponding to the following formula (V):

(V)

5. A process for the functionalization of a solid support comprising hydroxyl or hydride functional groups at the surface, said process comprising contacting said support is brought into contact with a solution comprising a silane compound as defined in claim 1.

6. The process of claim 5, comprising, before said contacting, treating the surface of the support in order to create, on the surface, the hydroxyl or hydride functional groups for the grafting.

7. The process of claim 5, wherein the solid support is an organic support or an inorganic support.

8. The process of claim 7, wherein the inorganic support is made of a metal oxide, a metal or silicon.

9. A method for the immobilization of a biological molecule on a solid support, successively comprising:
   implementing the process of claim 5 to obtain a support;
   b) contacting the support obtained in stage a) is brought into contact with a solution comprising the biological molecule to be immobilized.

10. The immobilization method of claim 9, wherein the biological molecule to be immobilized is selected from the group consisting of nucleic acids, polypeptides, lipids, carbohydrates and hormones.

11. The immobilization method of claim 9, wherein the biological molecule to be immobilized is a nucleic acid.

* * * * *